(12) United States Patent
He et al.

(10) Patent No.: US 7,646,847 B2
(45) Date of Patent: Jan. 12, 2010

(54) HANDHELD TWO-DIMENSIONAL X-RAY DIFFRACTOMETER

(75) Inventors: Bob B. He, Madison, WI (US); Roger D. Durst, Madison, WI (US)

(73) Assignee: Bruker AXS Inc., Madison, WI (US)

( * ) Notice: Subject to any disclaimer, the term of this patent is extended or adjusted under 35 U.S.C. 154(b) by 0 days.

(21) Appl. No.: 12/113,505

(22) Filed: May 1, 2008

(65) Prior Publication Data

US 2009/0274274 A1 Nov. 5, 2009

(51) Int. Cl.
*G01N 23/20* (2006.01)
(52) U.S. Cl. ......................................... 378/71
(58) Field of Classification Search ............. 378/70–90, 378/119, 140
See application file for complete search history.

(56) References Cited

U.S. PATENT DOCUMENTS

| | | | | |
|---|---|---|---|---|
| 4,388,728 | A * | 6/1983 | Emmanuel | 378/34 |
| 4,489,425 | A | 12/1984 | Borgonovi | |
| 6,353,656 | B1 | 3/2002 | LeVert et al. | |
| 6,442,236 | B1 * | 8/2002 | Utaka | 378/84 |
| 2007/0058779 | A1 * | 3/2007 | Yokhin et al. | 378/71 |

OTHER PUBLICATIONS

He, et al., "A New Method for Residual Stress Measurement Using An Area Detector", Proceedings of The Fifth International Conference on Residual Stresses (ICRS-5), pp. 634-639, Linkoping, Sweden, 1997.
He, Baoping Bob, "Computer Simulation of Diffraction Stress Measurements With 2D Detectors", Proceedings of the SEM Spring Conference on Experimental and Applied Mechanics, Jun. 1-3, 1998, Houston, Texas.
He, et al., "Fundamental Equation of Strain and Stress Measurement Using 2D Detectors", Proceedings of the SEM Spring Conference on Experimental and Applied Mechanics, Jun. 1-3, 1998, Houston, Texas.
He, et al., "Strain and Stress Measurement With a Two-Dimentional Detector", The 46th Annual Denver X-Ray Conference, Aug. 4-8, 1997, Steamboat Springs, Colorado.

* cited by examiner

*Primary Examiner*—Courtney Thomas
(74) *Attorney, Agent, or Firm*—Law Offices of Paul E. Kudirka (57) ABSTRACT

A handheld X-ray diffractometer comprises a miniaturized X-ray source and multiple area detectors to allow the diffractometer to obtain two-dimensional X-ray diffraction images in a large diffraction space without rotating the sample. The source and detectors are located inside of a radio opaque enclosure that protects the operator during use. The handheld diffractometer also comprises a sample monitoring and alignment system that allows an operator to observe the measuring area and to align the diffractometer to the sample from outside of the housing. A specially designed mouthpiece, which mates the diffractometer to the sample area, prevents x-ray leakage and triggers off the data collection. The detectors can be positioned to perform measurements necessary to calculate a mechanical stress in the sample. Linear detectors may also be used in place of the area detectors.

20 Claims, 6 Drawing Sheets

HANDHELD TWO-DIMENSIONAL X-RAY DIFFRACTOMETER

BACKGROUND

This invention relates to X-ray diffraction systems. X-ray diffraction is a non-destructive technique for the qualitative and quantitative analysis of crystalline material samples, which are generally provided in the form of powders or solids. In accordance with this technique, an X-ray beam is generated by an X-ray tube with a stationary anode, by a conventional rotating anode X-ray source or by a synchrotron source and directed toward the material sample under investigation. When the X-rays strike the sample, they are diffracted according to the atomic structure of the sample.

Figure 1:
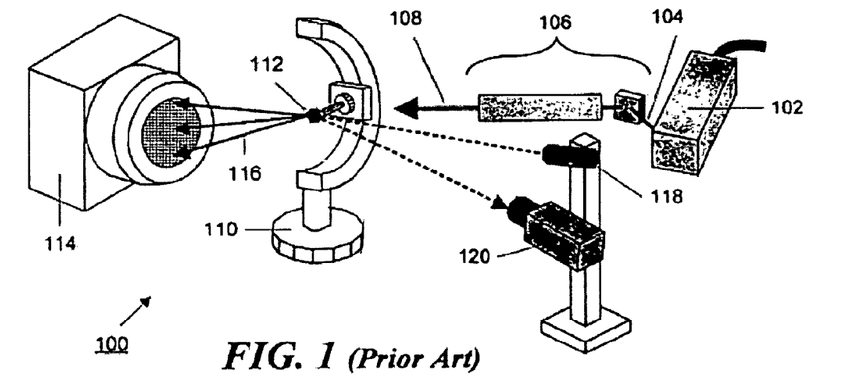
FIG. 1 is a perspective schematic view of a conventional laboratory X-ray diffraction system.

X-ray diffraction data can be collected using one-dimensional diffraction (1D) profiles and two-dimensional (2D) profiles. One dimensional profiles are measured by rotating the sample and detecting diffracted X-rays with scanning point detectors or linear position-sensitive detectors. Two-dimensional profiles are acquired with two-dimensional, or area, detectors and the resulting data is then processed using two-dimensional image processing and two-dimensional diffraction pattern manipulation and interpretation. A typical two-dimensional laboratory diffractometer system 100 normally consists of five components as shown in FIG. 1. The components include an X-ray source 102 that produces a primary X-ray beam 104 with the required radiation energy, focal spot size and intensity. X-ray optics 106 are provided to condition the primary X-ray beam 104 to a conditioned, or incident, beam 108 with the required wavelength, beam focus size, beam profile and divergence. A goniometer and stage 110 are used to establish and manipulate geometric relationships between the incident X-ray beam 108, the sample 112 and the X-ray detector 114. The incident X-ray beam 108 strikes the sample 112 and produces scattered X-rays 116 which are recorded in the detector 114. A sample alignment and monitor assembly comprises a sample illuminator 118, typically a laser, that illuminates the sample 112 and a sample monitor 120, typically a video camera, which generates a video image of the sample to assist users in positioning the sample in the instrument center and monitoring the sample state and position.

The two-dimensional detector 114 intercepts and records the scattered x-rays 116 from the sample 112, and saves and displays the diffraction pattern in a two-dimensional image frame.

In the laboratory, X-ray diffractometers can be used to determine crystal structure and identify compounds. During laboratory data collection, the sample and instrument components are typically moved. For example, the gonimeter is used to provide a data scan and to set a tilt angle between the incident X-ray beam and the sample. However, there are many applications that require a diffractometer to be used outside of the laboratory. For example, with in-situ stress measurements, the diffractometer must be brought to the location of the stressed member. Consequently, a portable or handheld X-ray diffractometer would be desirable. Such a handheld instrument must be light in weight, small in size and energy efficient. Aligning the instrument accurately to the sample spot to be measured is also critical to obtain accurate measurement results. However, the conventional laboratory instrument is not suitable for handheld use because the setup is bulky and large and, as set forth above, requires that the instrument components be moved during data collection. Further, it would be difficult to properly align the instrument to the sample spot.

SUMMARY

In accordance with the principles of the invention, a handheld X-ray diffractometer comprises a miniaturized X-ray source and multiple area detectors to allow the diffractometer to obtain two-dimensional X-ray diffraction images in a large diffraction space without rotating the sample.

In one embodiment, the source and detectors are inside of a radio opaque enclosure that protects the operator during use. The handheld diffractometer also comprises a sample monitoring and alignment system that allows an operator to observe the measuring area and to align the diffractometer to the sample from outside of the housing. A specially designed mouthpiece, which mates the diffractometer to the sample area, prevents x-ray leakage and triggers off the data collection.

In another embodiment, the a sample monitoring and alignment system is located within the safety enclosure and the video display is mounted outside the enclosure so that the operator can observe measuring sample surface, save images of measuring area, and align the system to the measuring area without exposure to X-rays.

In still another embodiment, the detectors are positioned to perform measurements necessary to calculate a mechanical stress in the sample. In particular, the detectors are positioned for measuring diffraction rings at predetermined tilt angles with respect to the sample and the incident X-ray beam. In addition, one detector is positioned to measure the diffraction from crystal planes nearly parallel to the sample surface.

In yet another embodiment, linear detectors are used in place of the area detectors.

DETAILED DESCRIPTION

Figure 2:
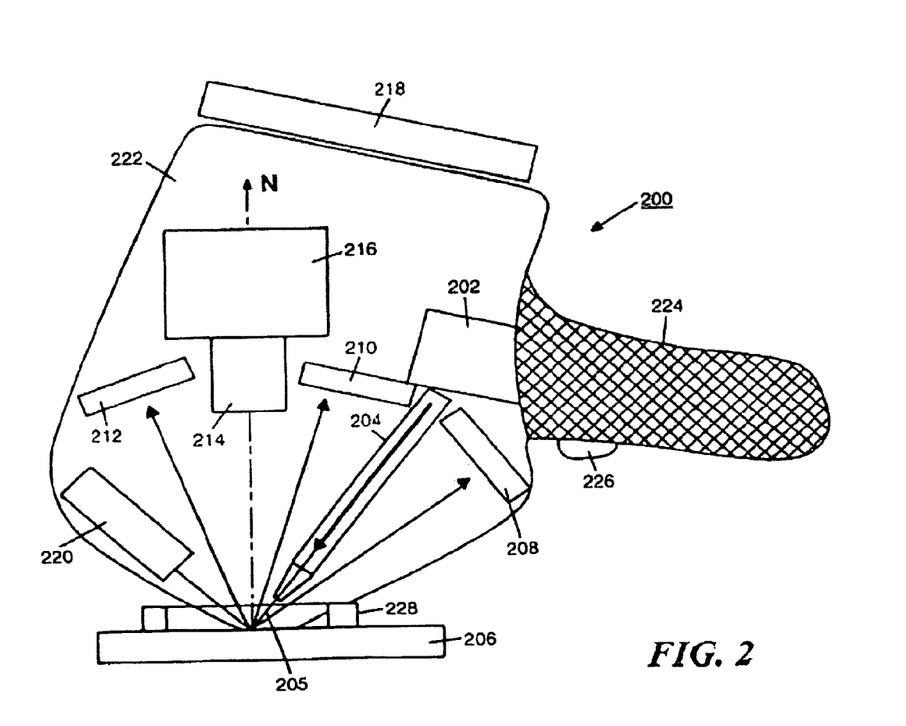
FIG. 2 is a partial cutaway schematic of the interior of a handheld X-ray diffractometer constructed in accordance with the principles of the invention.

FIG. 2 shows a partial cutaway schematic side view of a two-dimensional X-ray diffractometer 200 constructed in accordance with the principles of the invention. The diffractometer 200 comprises a miniaturized X-ray source 202 that produces X-rays with the required radiation energy, focal spot size and intensity. The construction of such an X-ray source is well-known and examples can be found in U.S. Pat. Nos. 5,621,780; 5,854,822 and 7,127,033, the disclosure of which is hereby incorporated by reference. The target material in the X-ray tube can be chromium, cobalt, iron, copper, molybdenum or other metals. The most critical requirement for the tube is energy efficiency because the entire system must be powered by a battery in order to make it portable. However, it is also necessary to delivery a high dosage of X-rays in a short period of time since the operator can only hold the system steady in a given position for a short time. One effective way to achieve both high energy efficiency and high x-ray dosage is run the x-ray source 202 at substantial power for a short time. Such operation is analogous to a flashing light in a camera.

X-ray optics 204 condition the primary x-ray beam (not shown in FIG. 2) to the required wavelength, beam focus size, beam profile and divergence. The X-ray optics 204 also direct the incident beam 205 on to the sample surface 206 at a predetermined incident angle. The X-ray beam generated from a typical X-ray tube has a broad spectrum distribution including K-alpha and K-beta lines. Typically K-alpha radiation is used for X-ray diffraction so that it is necessary to monochromatize the X-ray beam using a K-beta filter or monochromator. The K-beta filter can be inserted in any location within the X-ray beam path, including the primary and incident beams. In one embodiment, the window through which the primary X-ray beam emerges from the X-ray source is fabricated from K-beta filter material. In another embodiment the detector window is fabricated from K-beta filter material. If the K-beta filter material is used for X-ray source window, the X-ray beam will contain mainly K-alpha radiation. The X-ray beam can be collimated to a proper beam size and divergence by a pinhole collimator, a monocapillary or a polycapillary lens in a conventional fashion. Multiple two-dimensional, or area, X-ray detectors 208, 210 and 212 read the resulting diffraction pattern in three-dimensional space and a video microscope 214, video camera 216 and a video display 218 allow the operator to monitor the measured sample area and align the system precisely to the intended measurement spot without exposing the operator to X-ray radiation. A laser 220 generates a laser beam that provides a reference point on the sample surface 206 for precise sample alignment.

Several important safety elements are included. A radiation shield 222 forming a safety enclosure covers all the space and components exposed to the direct beam 204 of the X-ray source and scattered X-rays from sample surface 206 and other components. A handle or support 224 allows the operator to position the system and an operation trigger 226 can be actuated to start data collection. A nosepiece 228 provides a safety interlock. The nosepiece 228 has an interlock mechanism (not shown in FIG. 2) to ensure that X-rays can be released from the X-ray source 202 only if the sample surface 206 is securely covered by the nosepiece 228. The nosepiece 228 can be configured to establish different angles at which the incident X-ray beam 205 is incident on the sample surface 206 and also formed to fit different sample surface shapes. The safety interlock switch may also trigger off x-ray diffraction data collection in conjunction with the trigger 226. The nosepiece 228 may include several exchangeable parts, each of which matches a particular surface shape, such as a flat surface, a cylindrical surface or a corner. The nosepiece can also be designed to control the x-ray incident angle for different metal types to optimize the measurement condition. An oscillation mechanism may be integrated to the nosepiece to improve the measurement sampling when dealing with samples of large grain structure. A magnetic nosepiece may be used to enhance the stability of the measurement position when measuring a sample of ferrous materials.

The multiple X-ray area detectors 208, 210 and 212 eliminate the necessity to move sample and instrument components during data collection and, consequently, the inventive apparatus does not need to provide data scan motion or to change tilt angles during data collection. Therefore, the gonistat used by laboratory systems and many existing portable systems to provide the data scan and to set tilt angles can be eliminated, reducing the weight and size of the apparatus.

Figure 3:
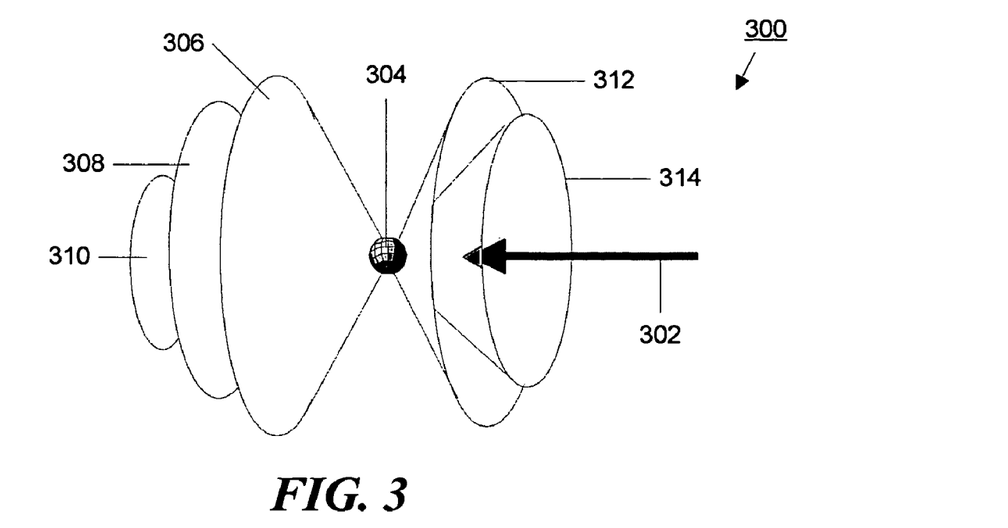
FIG. 3 is a schematic diagram showing diffraction cones illustrating the paths of diffracted X-rays produced when an X-ray beam impinges on a crystalline sample.

One embodiment of the inventive handheld diffractometer is particularly useful in on-site stress measurements. FIG. 3 shows a typical pattern 300 of diffracted x-rays from a polycrystalline (powder) sample 304. The diffraction pattern 300 from such a sample 304 forms a series of diffraction cones 306-314 if a large number of crystals are oriented randomly in the space covered by the incident X-ray beam 302. Each diffraction cone, such as cone 306, corresponds to paths followed by diffracted X-rays that are diffracted from the same family of crystalline planes in all the participating crystals. Polycrystalline materials can be single-phase or multi-phase solids.

Figure 4:
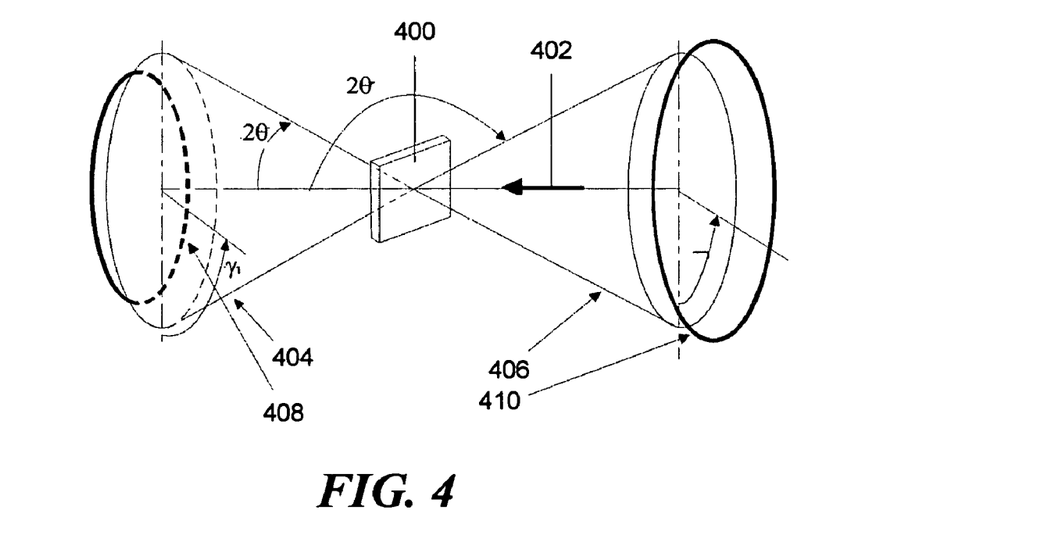
FIG. 4 is a schematic diagram showing distortion of diffraction cones caused by mechanical stress in the sample.

Stress measurement with two dimensional X-ray detectors is based on a fundamental relationship between the stress tensor and diffraction cone distortion as shown in FIG. 4. This figure shows two diffraction cones 404 and 406 that are produced when an X-ray beam 402 strikes a sample 400. Stresses in sample 400 distort the diffraction cone shape so that the Bragg angle 2θ becomes a function of the angle γ (that is, 2θ=2θ(γ)) where the particular function is uniquely determined by the stress tensor and the sample orientation. In particular, cones 404 and 406 are distorted to form cones 408 and 410, respectively. The fundamental equation for stress measurement using two-dimensional X-ray detectors is given as:

$$p_{11}\sigma_{11} + p_{12}\sigma_{12} + p_{13}\sigma_{13} + p_{22}\sigma_{22} + p_{23}\sigma_{23} + p_{33}\sigma_{33} = \ln\left(\frac{\sin\theta_0}{\sin\theta}\right)$$

$$\text{where } p_{ij} = \begin{cases} (1/E)[(1+v)f_{ij} - v] = \frac{1}{2}S_2 f_{ij} + S_1 & \text{if } i = j \\ (1/E)(1+v)f_{ij} = \frac{1}{2}S_2 f_{ij} & \text{if } i \neq j \end{cases}$$

$$\text{and } \begin{matrix} f_{11} = h_1^2 & f_{12} = 2h_1 h_2 & f_{22} = h_2^2 \\ f_{13} = 2h_1 h_3 & f_{23} = 2h_2 h_3 & f_{33} = h_3^2 \end{matrix}$$

and $h_1$=sin θ(sin φ sin ψ sin ω+cos φ cos ω)+cos θ cos γ sin φ cos ψ−cos θ sin γ(sin φ sin ψ cos ω−cos φ sin ω)

$h_2$=−sin θ(cos φ sin ψ sin ω−sin φ cos ω)−cos θ cos γ cos φ cos ψ+cos θ sin γ(cos φ sin ψ cos ω+sin φ sin ω)

$h_3$=sin θ cos ψ sin ω−cos θ sin γ cos ψ cos ω−cos θ cos γ sin ψ

The $f_{ij}$'s are the strain coefficients determined by {$h_1$, $h_2$, $h_3$} which are components of the unit vector of the diffraction vector expressed in the sample coordinates. The term ln(sin $θ_0$/sin θ) represents the diffraction cone distortion at a particular (γ, 2θ) position. $S_1$ and $S_2$ are the macroscopic elastic constants. The ω, ψ and φ angles refer to a sample orientation in an Eulerian gonistat.

Since the stress measurement is based on a variation of the interplanar spacing of the crystals due to stresses, knowledge of the lattice parameters without the influence of stresses is critical. Conventionally, this information is obtained by the extrapolation of data measured at other tilt angles. This extrapolation is acceptable if a linear relation is maintained between the strain and $\sin^2 \psi$ where $\psi$ is the tilt angle between the normal of the measured crystal planes and the normal of the sample surface. However, this linear relation does not hold true if there are preferred orientation, large crystal grains or stress gradients in the sample. Therefore, prior art stress measurement systems cannot be used with accuracy in many applications.

In accordance with the principles of the invention, information regarding lattice parameters without the influence of stresses is obtained by measurement directly on the sample surface. Based on the mechanics, the stress component normal to the sample surface is zero or negligible. The inventive system measures a part of a diffraction ring from a crystal plane, the normal of which is very close to the normal of the sample surface.

Figure 5:
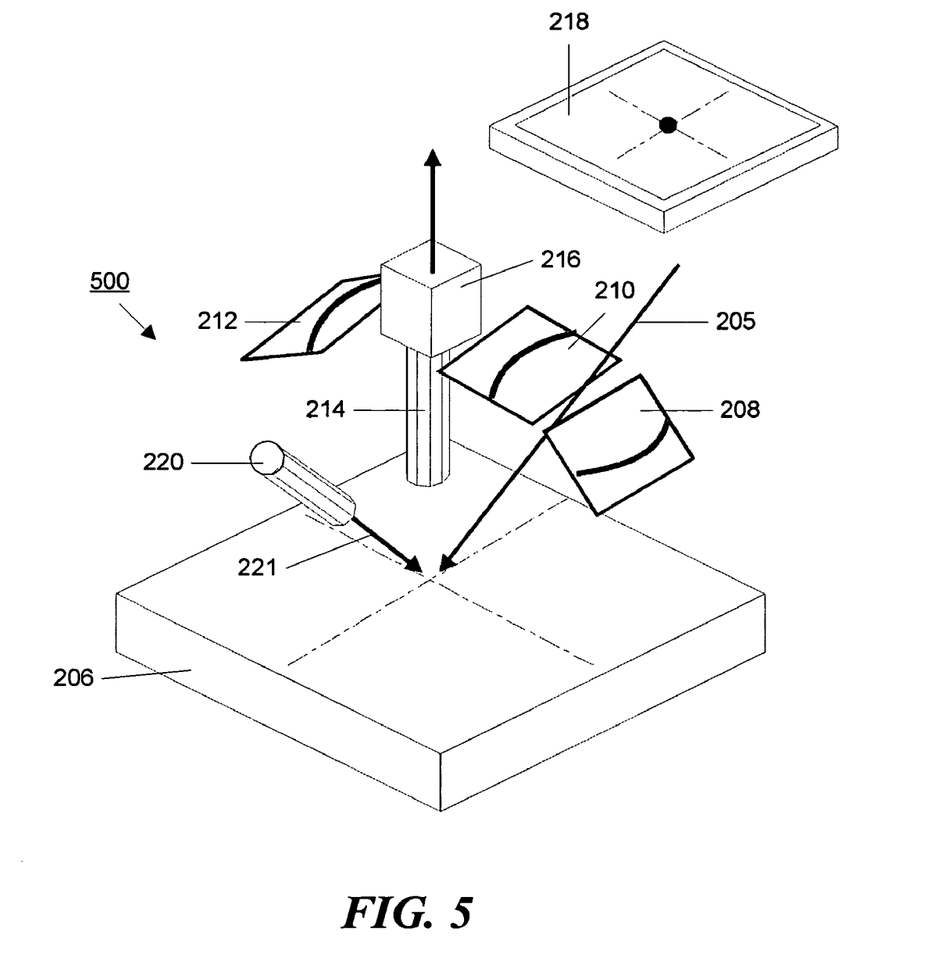
FIG. 5 is a three-dimensional cutaway view of the inventive handheld diffractometer showing a detector arrangement suitable for measuring stress in a sample.

FIG. 5 shows an interior configuration 500 of an embodiment of the inventive handheld diffractometer suitable for stress measurement in a three-dimensional view. The primary x-ray beam 205 hits the sample 206 at a predetermined tilt angle. The diffraction ring produced by a predetermined crystal plane is sensed by the two-dimensional X-ray detectors 208 and 210. The diffraction ring distortion is analyzed by the computer to output the residual stress result. The two-dimensional detector 212 measures a part of a diffraction ring from another crystal plane, the normal of which is very close to the normal of the sample surface 206 so a stress-free crystal lattice parameter can be measured directly from the sample surface 206. In another words, detector 212 detects X-rays diffracted from crystal planes which are nearly parallel to the sample surface 206. The stress-free crystal lattice parameter is used in the stress calculation and this additional data improves the accuracy and reliability of the stress results.

Figure 6:
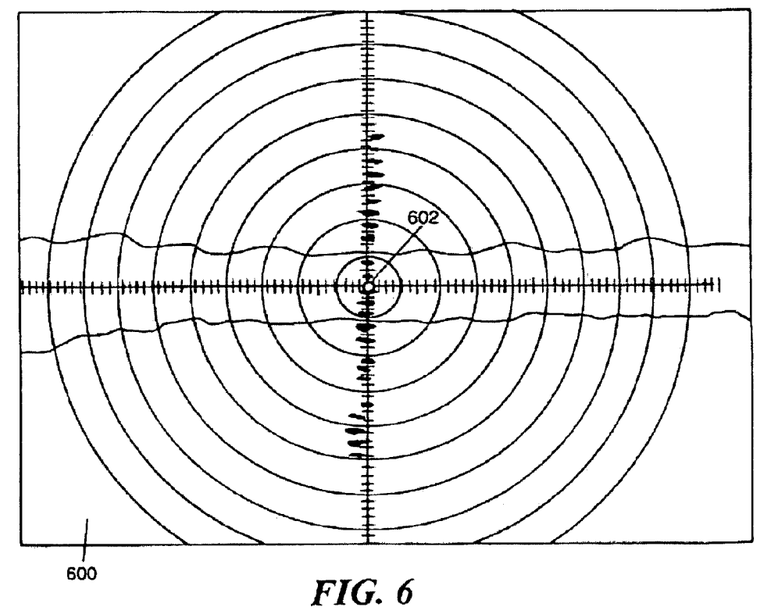
FIG. 6 is a screen shot of a video display of a view through a video microscope showing a magnified image of a metal sample surface with a laser spot on the center.

Another important consideration for measuring x-ray diffraction data with a handheld system is that the measurement surface must be covered by the system during the data collection for safety reasons. However, it is critical to be able to observe the measurement surface and align the system accurately to the sample surface. The inventive system uses a laser beam to provide a reference on the sample surface, and a video microscope with a display located outside of the radiation enclosure to allow the operator to observe the system alignment and to keep the system aligned to the sample surface. For example, in FIG. 5, laser beam 515 generated by laser 220 provides a reference to the position of the sample 206. The position of the laser spot on the sample 206 can be observed by a video system including the microscope 214, camera 216 and video display 218. The laser spot will appear in the center of a crosshair if the sample 206 is at the correct position to make a measurement. When the x-ray beam 205 is aimed at the sample 206 and diffraction data is being collected, the sample measurement area 206 is covered by the system enclosure to prevent leakage of X-rays for the safety of operator. Therefore, a video system must be provided to align the system accurately to the sample surface 206. The video microscope 216 also allows an image of the measurement area to be linked to the x-ray diffraction data. FIG. 6 is such an image of magnified metal sample surface 600 with a laser spot 602 on the center.

Figure 7:
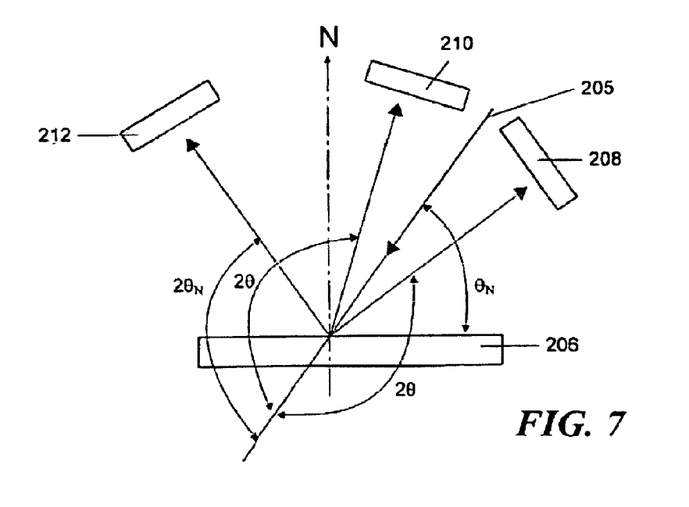
FIG. 7 is a partial side view of the inventive handheld diffractometer illustrating angles at which the X-ray detectors may be positioned for stress measurements.

FIG. 7 shows a partial side view of FIG. 5. In one embodiment, detectors 208 and 210 measure X-rays diffracted from a set of crystal planes with 2θ angles in the range 120°-170° where the angle depends on the incident X-ray beam 205 wavelength and the metal type of the sample 206. The detector 212 measures diffraction from a different set of crystal planes with a $2\theta_N$ angle in the range 60°-90°. Both sets of the crystal planes represent different crystal orientations. Therefore, the diffraction data from both sets of crystal planes also contains information on anisotropic features of the crystals.

The following table gives possible diffraction angle selections for four pure metal samples if Co-Kα incident X-ray radiation is used. One skilled in the art can also determine other possible angles if different radiation is used and different metals are measured.

| | Co-Kα radiation | |
| --- | --- | --- |
| Metal-Alloy | 2θ | $2\theta_N$ |
| α-Fe | 161.4 | 77.2 |
| Al | 162.0 | 77.4 |
| α-Ti | 154.2 | 74.7 |
| Cu | 163.5 | 88.8 |

Figure 8:
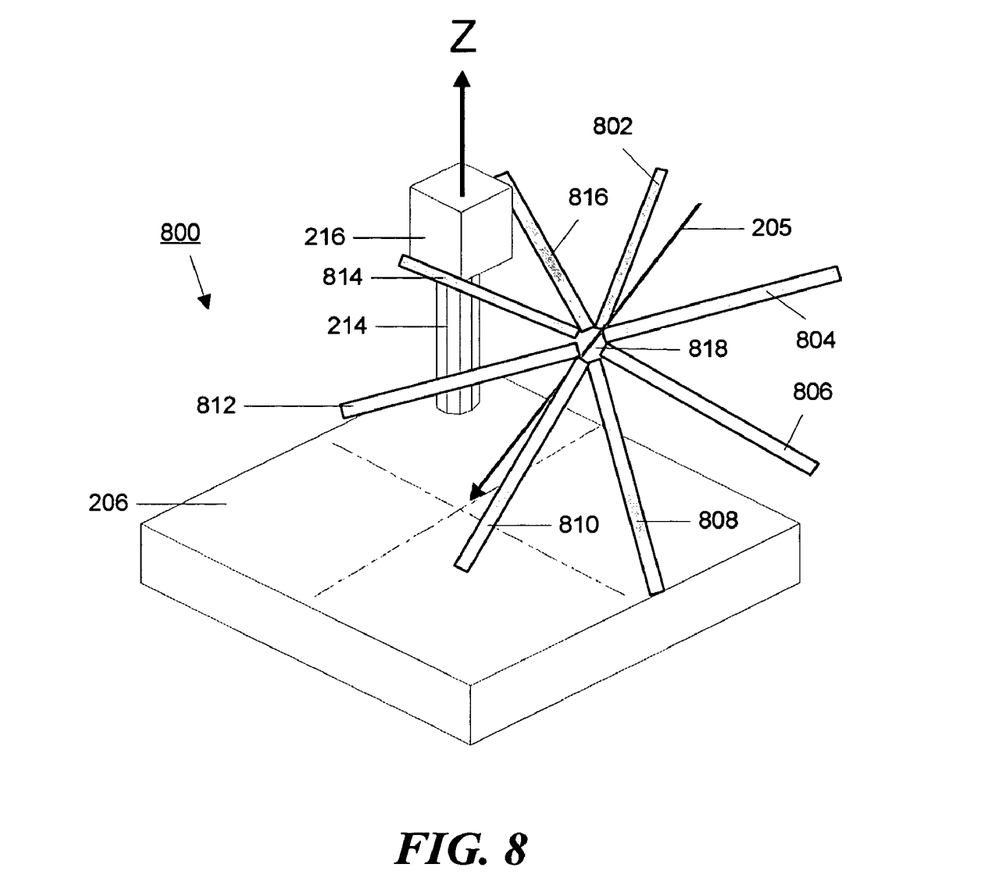
FIG. 8 is a partial schematic view of an inventive handheld X-ray diffractometer that uses linear X-ray detectors in place of area X-ray detectors.

FIG. 8 shows a configuration 800 that is an alternative to the configuration 500 in FIG. 5. In this alternative configuration, eight linear X-ray detectors (802-816) are used. The detectors are arranged in a radial pattern around a center opening 818 through which the incident X-ray beam 205 passes. Adjacent linear detectors are separated by a 45° angle. The incident X-ray beam 205 hits the sample 206 at a predetermined tilt angle to produce diffracted X-rays. The eight detectors 802-816 measure eight points on a diffraction ring produced by diffraction from a predetermined crystal plane. The diffraction ring distortion is analyzed by a computer to generate the residual stress result. One skilled in the art would also understand the possibility and motivation to use less or more linear detectors in order to balance cost and sampling statistics. The other features described in the previous configuration also apply to this configuration.

Figure 9:
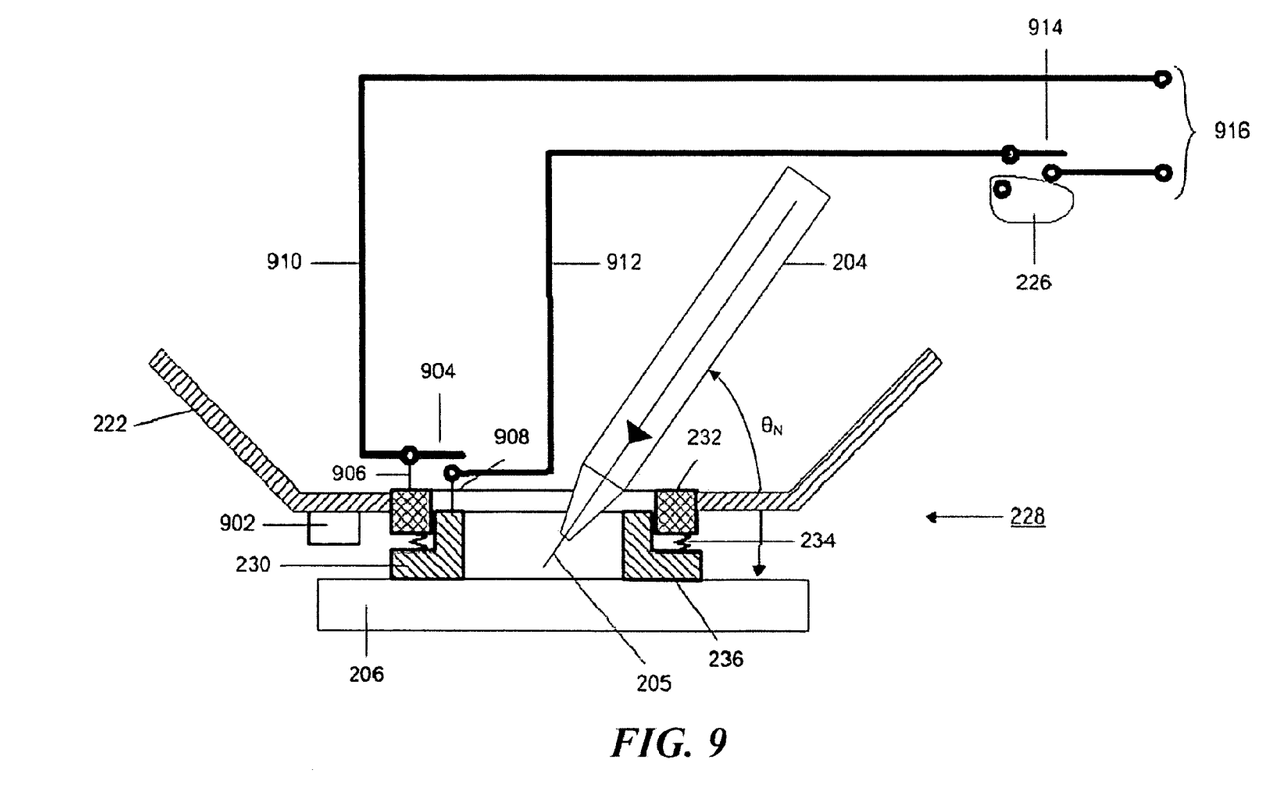
FIG. 9 is a schematic diagram illustrating details of a nosepiece with an interlock mechanism.

FIG. 9 is a schematic cross-sectional diagram of an illustrative nosepiece structure 228. The nosepiece 228 has an x-ray labyrinth consisting of the interleaved labyrinth rings 230 and 232 and a spring ring 234. Labyrinth ring 232 is sealed to the radiation shield 222. Labyrinth ring 230 is connected to labyrinth ring 232 by means of a spring ring 234 so that labyrinth ring 230 can slide relative to labyrinth ring 232. In operation when the unit is brought into contact with the sample 206, the bottom plane 236 of labyrinth ring 230 is brought into close contact with the sample 206 to prevent x-ray leakage when x-ray beam 206 passing through X-ray optics 204 hits the sample 206.

An interlock switch 904 is provided which is connected by support 906 to labyrinth ring 232 and by support 908 to labyrinth ring 230. When labyrinth ring 230 is tightly pressed against the sample 206, the force compresses the spring ring 234 and closes the interlock switch 904. The interlock switch 904 is connected by conductors 910 and 912 to trigger switch 914 and further connected to the x-ray source control (not shown in FIG. 9) via terminals 916. Trigger switch 914 is actuated when trigger 226 is depressed by an operator. Only when both the interlock switch 904 and the trigger switch 914 are closed, can the x-ray source operate. A radiation sensor 902 may be installed in the outside of the radiation shield 222 and next to the contacting surface 236 between the sample 206 and the labyrinth ring 230 so that any x-ray leakage can be detected and the unit switched off.

Such a nosepiece structure can cover the surface of the measuring area to prevent the leakage of x-rays during the measurement so that no x-ray leakage is beyond a safe level. It is also possible to integrate a radiation sensor directly into the nosepiece 228 so that that the dosage of any leaked x-rays is monitored. One skilled in the art could anticipate that the nosepiece may be designed to fulfill several other functions. For example, labyrinth ring 230 may comprise several exchangeable parts of which each matches a particular sample surface shape, such as flat, cylinder or corners. Labyrinth ring 230 may be made of magnetic material to enhance the stability of the measurement position when measuring a sample composed of ferrous materials.

Further, nosepiece 228 can also be designed to control the x-ray incident angle $\theta_N$ for different metal types to optimize the measurement condition. An oscillation mechanism (not shown in FIG. 9) may be integrated to the nosepiece 228 to improve the measurement sampling when dealing with samples of large grain structure.

While the invention has been shown and described with reference to a number of embodiments thereof, it will be recognized by those skilled in the art that various changes in form and detail may be made herein without departing from the spirit and scope of the invention as defined by the appended claims. For example, in other embodiments, the system may contain a level sensor to help orient the handheld system relative to the sample or structure. The system may further contain a Global Position System receiver to record the geographic location of each measurement. It may also be beneficial to have several handheld units linked each other or to a station through wireless technologies. One skilled in the art can also see the possibility and motivation to modify the system so that it can be mounted permanently on critical locations of structures so that the residual stress and surface condition are remotely and constantly or frequently monitored.

What is claimed is:

1. A handheld X-ray diffractometer for making measurements on an area of a sample, the diffractometer comprising:
    a miniature X-ray source for generating a primary X-ray beam;
    X-ray optics for conditioning the primary X-ray beam to produce an incident X-ray beam;
    a plurality of two-dimensional X-ray area detectors positioned at fixed locations with respect to the incident X-ray beam; and
    a housing enclosing the X-ray source, the X-ray optics and the X-ray detectors, the housing, X-ray source, the X-ray optics and the X-ray detectors being of a size and weight to allow an operator to hold the diffractometer while making a measurement.

2. The diffractometer of claim 1 wherein the housing is radio opaque.

3. The diffractometer of claim 1 further comprising a sample monitoring and alignment system that allows an operator to observe the sample area and to align the diffractometer to the sample area from outside of the housing.

4. The diffractometer of claim 3 wherein the sample monitoring and alignment system comprises a video microscope located within the housing and a video display located outside the housing.

5. The diffractometer of claim 1 wherein the housing comprises a nosepiece, which mates the diffractometer to the sample area in order to prevent x-ray leakage.

6. The diffractometer of claim 5 wherein the nosepiece comprises a pair of interleaved labyrinth rings, one of which mates to the sample area and the other of which is attached to the housing, the labyrinth rings being connected by a flexible spring ring.

7. The diffractometer of claim 6 wherein the one labyrinth ring is shaped to closely conform to the sample area shape.

8. The diffractometer of claim 1 wherein the two-dimensional X-ray detectors are positioned to perform measurements necessary to calculate a mechanical stress in the sample at the sample area.

9. The diffractometer of claim 8 wherein detectors are positioned for measuring diffraction rings at predetermined tilt angles with respect to the sample and the incident X-ray beam and at least one detector is positioned to measure the diffraction from crystal planes nearly parallel to a surface of the sample.

10. The diffractometer of claim 1 wherein the X-ray source has a window though which the primary X-ray beam emerges and wherein the window is fabricated from K-beta filtering materials so that the primary X-ray beam consists of substantially K-alpha X-rays.

11. A handheld X-ray diffractometer for making measurements on an area of a sample, the diffractometer comprising:
    a miniature X-ray source for generating a primary X-ray beam;
    X-ray optics for conditioning the primary X-ray beam to produce an incident X-ray beam;
    a plurality of two-dimensional X-ray area detectors positioned at fixed locations with respect to the incident X-ray beam; and
    a housing enclosing the X-ray source, the X-ray optics and the X-ray detectors, the housing, X-ray source, the X-ray optics and the X-ray detectors being of a size and weight to allow an operator to hold the diffractometer while making a measurement.

12. The diffractometer of claim 11 wherein the housing is radio opaque.

13. The diffractometer of claim 11 further comprising a sample monitoring and alignment system that allows an operator to observe the sample area and to align the diffractometer to the sample area from outside of the housing.

14. The diffractometer of claim 13 wherein the sample monitoring and alignment system comprises a video microscope located within the housing and a video display located outside the housing.

15. The diffractometer of claim 11 wherein the housing comprises a nosepiece, which mates the diffractometer to the sample area in order to prevent x-ray leakage.

16. The diffractometer of claim 15 wherein the nosepiece comprises a pair of interleaved labyrinth rings, one of which mates to the sample area and the other of which is attached to the housing, the labyrinth rings being connected by a flexible spring ring.

17. The diffractometer of claim 16 wherein the one labyrinth ring is shaped to closely conform to the sample area shape.

18. The diffractometer of claim 11 wherein the two-dimensional X-ray area detectors are positioned to perform measurements necessary to calculate a mechanical stress in the sample at the sample area.

19. The diffractometer of claim 18 wherein detectors are positioned for measuring diffraction rings at predetermined tilt angles with respect to the sample and the incident X-ray beam and at least one detector is positioned to measure the diffraction from crystal planes nearly parallel to a surface of the sample.

20. An X-ray source for generating a monochromatic beam of K-alpha X-rays comprising:
    an X-ray source that generates an X-ray beam containing K-alpha and K-beta X-rays;
    a radio opaque housing surrounding the X-ray source; and
    an X-ray window in the housing through which the X-ray beam passes, the window being fabricated from K-beta filter materials so that X-rays emerging from the window are primarily K-alpha X-rays.

* * * * *